US008436136B2

(12) United States Patent
Henot et al.

(10) Patent No.: US 8,436,136 B2
(45) Date of Patent: May 7, 2013

(54) PEPTIDE COMPLEX

(75) Inventors: Frederic Henot, Brussels (BE); Thierry Legon, Korbeek Lo (BE); Isabelle Galy-Fauroux, Brussels (BE); Jean Duchateau, Soignies (BE)

(73) Assignee: Biotech Tools S.A., Brussels (BE)

( * ) Notice: Subject to any disclaimer, the term of this patent is extended or adjusted under 35 U.S.C. 154(b) by 492 days.

(21) Appl. No.: 10/557,334

(22) PCT Filed: May 18, 2004

(86) PCT No.: PCT/EP2004/005316
§ 371 (c)(1),
(2), (4) Date: Jul. 5, 2006

(87) PCT Pub. No.: WO2004/104026
PCT Pub. Date: Dec. 2, 2004

(65) Prior Publication Data
US 2006/0270833 A1 Nov. 30, 2006

Related U.S. Application Data

(60) Provisional application No. 60/472,131, filed on May 21, 2003.

(30) Foreign Application Priority Data

May 21, 2003 (EP) .................................. 03011498
Mar. 23, 2004 (EP) .................................. 04006900

(51) Int. Cl.
*A61K 38/28* (2006.01)
*C07K 5/00* (2006.01)
*C07K 7/00* (2006.01)
*C07K 16/00* (2006.01)
*C07K 17/00* (2006.01)
*A61P 5/50* (2006.01)

(52) U.S. Cl.
USPC .......................................... 530/303; 514/6.5

(58) Field of Classification Search .................. None
See application file for complete search history.

(56) References Cited

U.S. PATENT DOCUMENTS

| 3,907,765 | A | 9/1975 | Wang |
| 4,029,642 | A | 6/1977 | Obermeier |
| 6,312,711 | B1 | 11/2001 | Duchateau et al. |
| 7,247,712 | B2 * | 7/2007 | Tian et al. ............... 530/402 |
| 2002/0068715 | A1 | 6/2002 | Steinman et al. |
| 2003/0049797 | A1 * | 3/2003 | Yuki et al. ............... 435/69.7 |

FOREIGN PATENT DOCUMENTS

| SU | 1147010 A * | 12/1985 |
| WO | WO 90/14835 A1 | 12/1990 |
| WO | WO 97/06685 A1 | 2/1997 |
| WO | WO-97/28191 | 8/1997 |
| WO | WO 97/34002 A1 | 9/1997 |
| WO | WO 01/70772 A2 | 9/2001 |
| WO | WO 01/79259 A1 | 10/2001 |
| WO | WO 02/099061 A2 | 12/2002 |
| WO | WO 2004/104026 A1 | 12/2004 |

OTHER PUBLICATIONS

GenBank Accession No. AAA59172.1, 2001, pp. 1-2.*
Ploix et al., 1999, Diabetes, vol. 48: 2150-2156.*
Espinal, 1989, Understanding insulin action, pp. 19-21, Shoelson et al., 1992, Biochemistry, vol. 31: 1757-1767.*
Liddell, 2002, Ency. Life. Sci. pp. 1-6 Campbell, 1984, monoconal antiboidy technology, pp. 1-32.*
Unson et al., 1996, PNAS, vol. 93: 310-315.*
Perraut et al., 1993, Clin. Exp. Immunol. vol. 93: 382-386.*
Tobian et al., 2005. J. Immunol. vol. 174: 5209-5214.*
Martin et al., 2005, Bioinform. vol. 21: 218-226.*
Al-Sabbagh et al., 1994, Eur. J. Immunol. vol. 24: 2104-2109.*
Auger, I., et al., "HLA-DR4 and HLA-DR10 motifs that carry susceptibility to rheumatoid arthritis bind 70-kD heat shock proteins," *Nat. Med.* 2:306-310, Nature Publishing Company (1996).
Becker, T., et al., "CD40, an extracellular receptor for binding and uptake of Hsp70-peptide complexes," *J. Cell. Biol.* 158:1277-1285, The Rockefeller University Press (2002).
Cwiklinska, H., et al., "Heat shock protein 70 associations with myelin basic protein and proteolipid protein in multiple sclerosis brains," *Intl. Immunol.* 15:241-249, Oxford University Press (Feb. 2003).
Galazka, G., et al., "Effect of Hsp70-peptide complexes generated in vivo on modulation EAE," in *Progress in Basic and Clinical Immunology*, Mackiewicz et al., eds., Kluwer Academic/Plenum Publishers, New York, pp. 227-230 (2001).

(Continued)

*Primary Examiner* — Amy Juedes
(74) *Attorney, Agent, or Firm* — Venable LLP; Nancy J. Axelrod; Michael A. Gollin

(57) ABSTRACT

A complex comprising at least one heat shock protein (HSP) and at least one peptide selected from the group consisting of $R_1$-QXRAA-$R_2$ with $R_1$=peptide with 1-10 amino acids $R_2$=peptide with 1-10 amino acids X=K or R GFFYTPK (insulin 23-29) SEQ ID No 1 GFFYTPKT (insulin 23-30) SEQ ID No 2 IYPPNANK (DER p1) SEQ ID No 3 GIEYIQHNGVVQESYYR (DER P1) SEQ ID No 4 ASTTT-NYT (gp120 of HIV) SEQ ID No 5 DYEYLINVIHAFQYV (PLP 56-70) SEQ ID No 6 EKLIETYFSKNYQDYEYLINVI (PLP 43-64) SEQ ID No 7 KTTICGKGLSATVT (PLP 104-117) SEQ ID No 8 HSLGKWLGHPDKF (PLP 139-151 C140 ô S140) SEQ ID No 9 PRHPIRVELPCRISP (MOG 8-22) SEQ ID No 10 DEGGYTCFFRDHSYQ (MOG 92-106) SEQ ID No 11 Ac-ASQKRPSQRHG (MBP ac1-11) SEQ ID No 12 TGILDSIGRFFSG (MBP 35-47) SEQ ID No 13 VHFFKNIVTPRTP (MBP 89-101) SEQ ID No 14 HCLGKWLGHPDKF (PLP 139-151) SEQ ID No 15 MEVGWYRSPFSRVVHLYRNGK (MOG) SEQ ID No 16 QKRAAYDQYGHAAFE (*E. Coli* DnaJ) SEQ ID No. 17 QKRAAVDTYCRHNYG (HLA DRB1*0401) SEQ ID No. 18 QRRAAYDQYGHAAFE SEQ ID No. 19 and QRRAAVDTYCRHNYG SEQ ID No. 20.

9 Claims, 7 Drawing Sheets

OTHER PUBLICATIONS

Inouye, K., et al., "Enzyme-Assisted Semisynthesis of Human Insulin," Journal of the American Chemical Society, vol. 101, No. 3, 1979, pp. 751-752.

European Search Report, Application No. 04733537.7, mailed Sep. 4, 2007 (4 pages).

Amor et al., "Encephalitogenic Epitopes of Myelin Basic Protein, Proteolipid Protein, and Myelin Oligodendrocyte Glycoprotein for Experimental Allergic Encephalomyelitis Induction in Biozzi ABH (H-2AG7) Mice Share an Amino Acid Motif", Journal of Immunology, vol. 56, No. 8, pp. 3000-3008 (1996).

Chen et al., "Enhancement of DNA Vaccine Potency by Linkage of Antigen Gene to ANHSP70 Gene" Cancer Research, American Association for Cancer Research, vol. 60, pp. 1035-1042 (2000).

European Search Report dated Feb. 22, 2011, issued in corresponding European Patent Application No. 10181570.

* cited by examiner

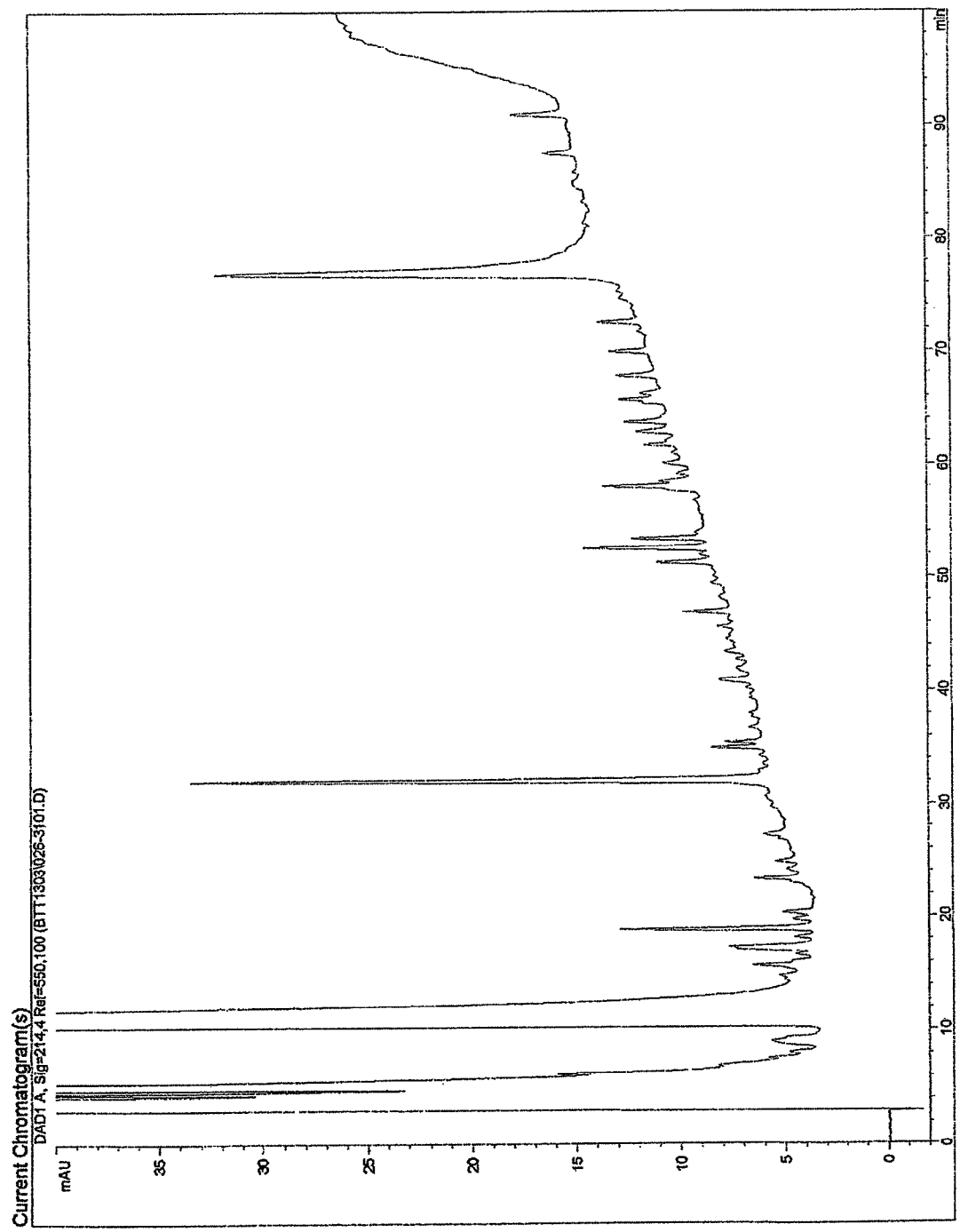
Fig.1.1

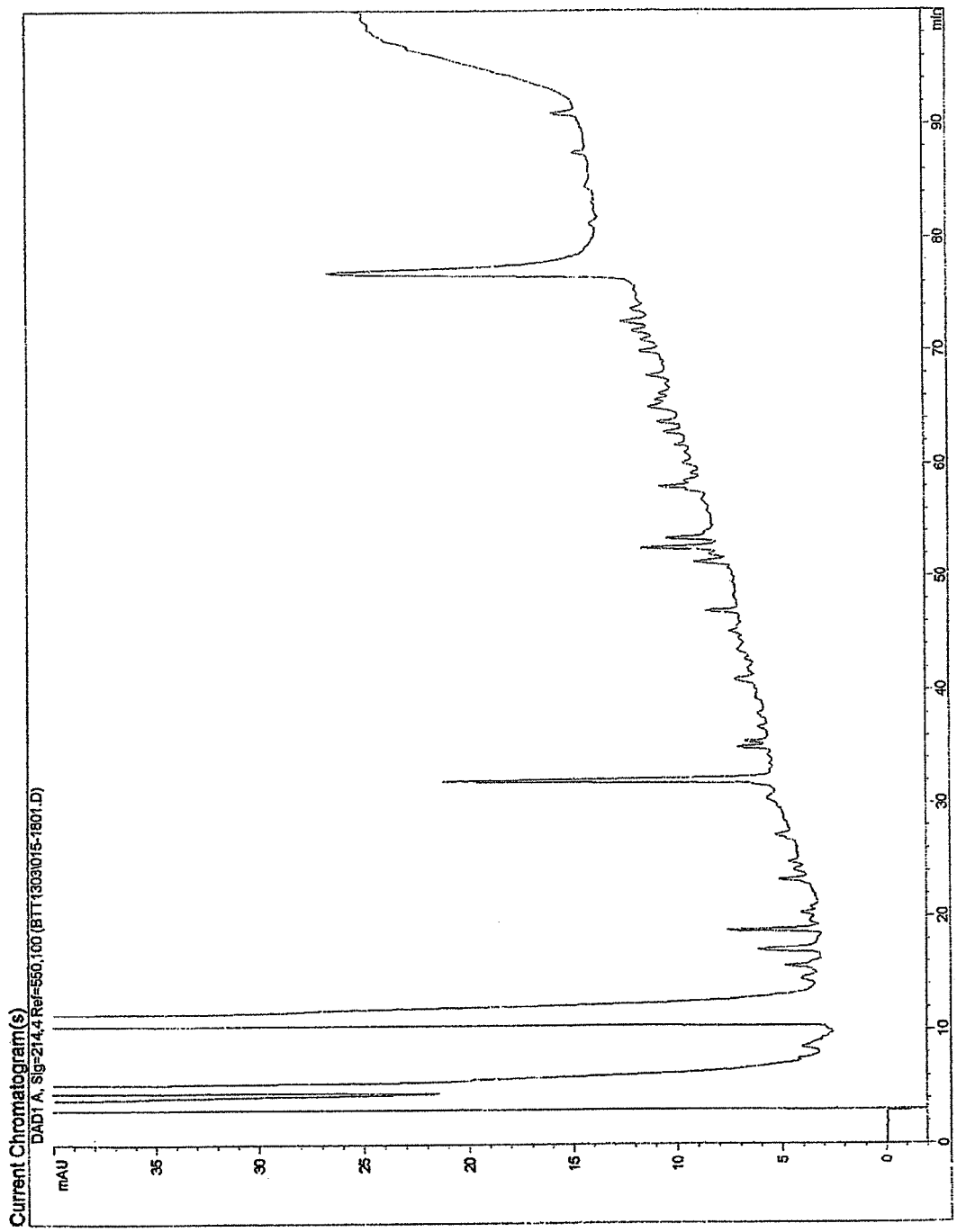
Fig.1.2

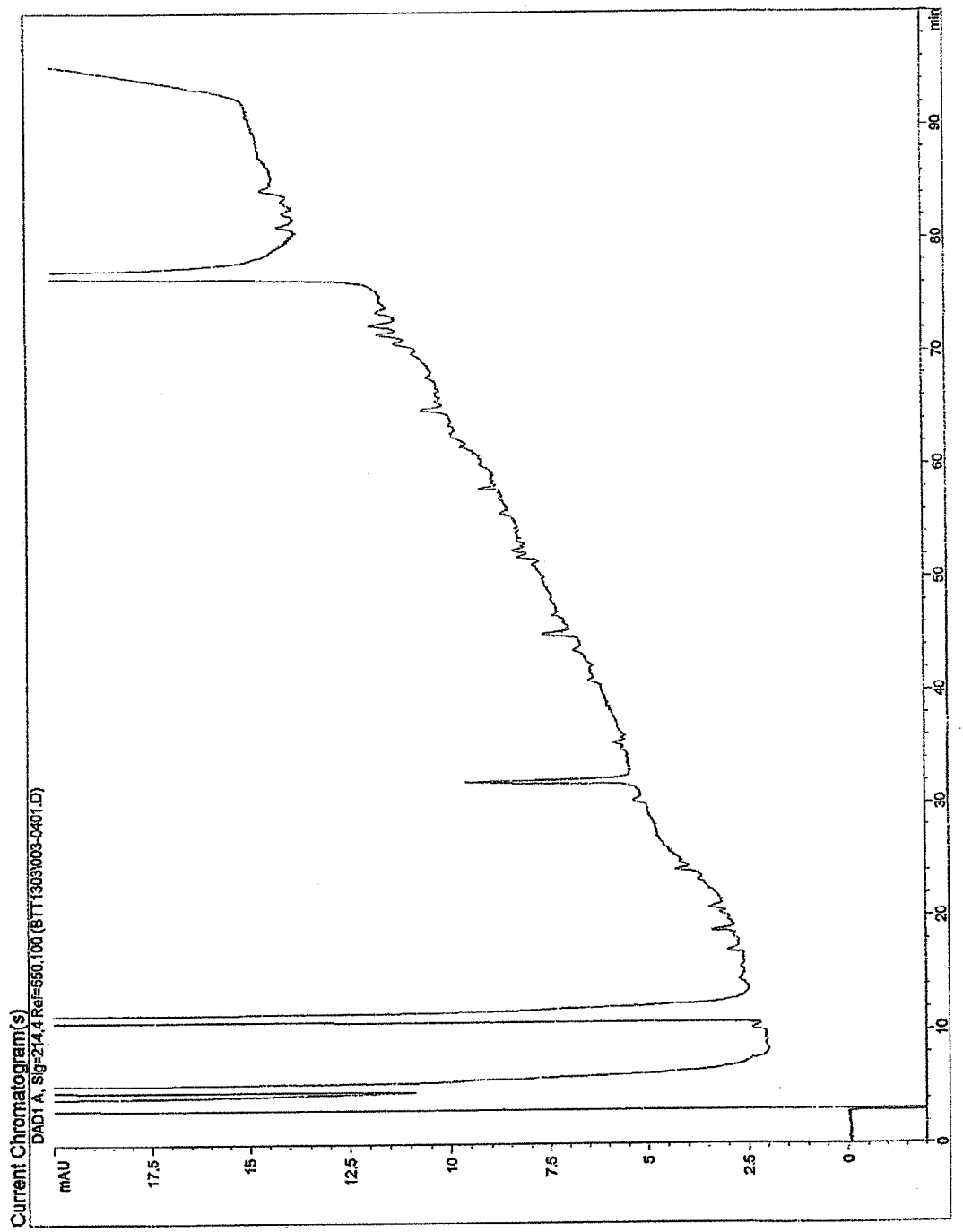
Fig. 1.3

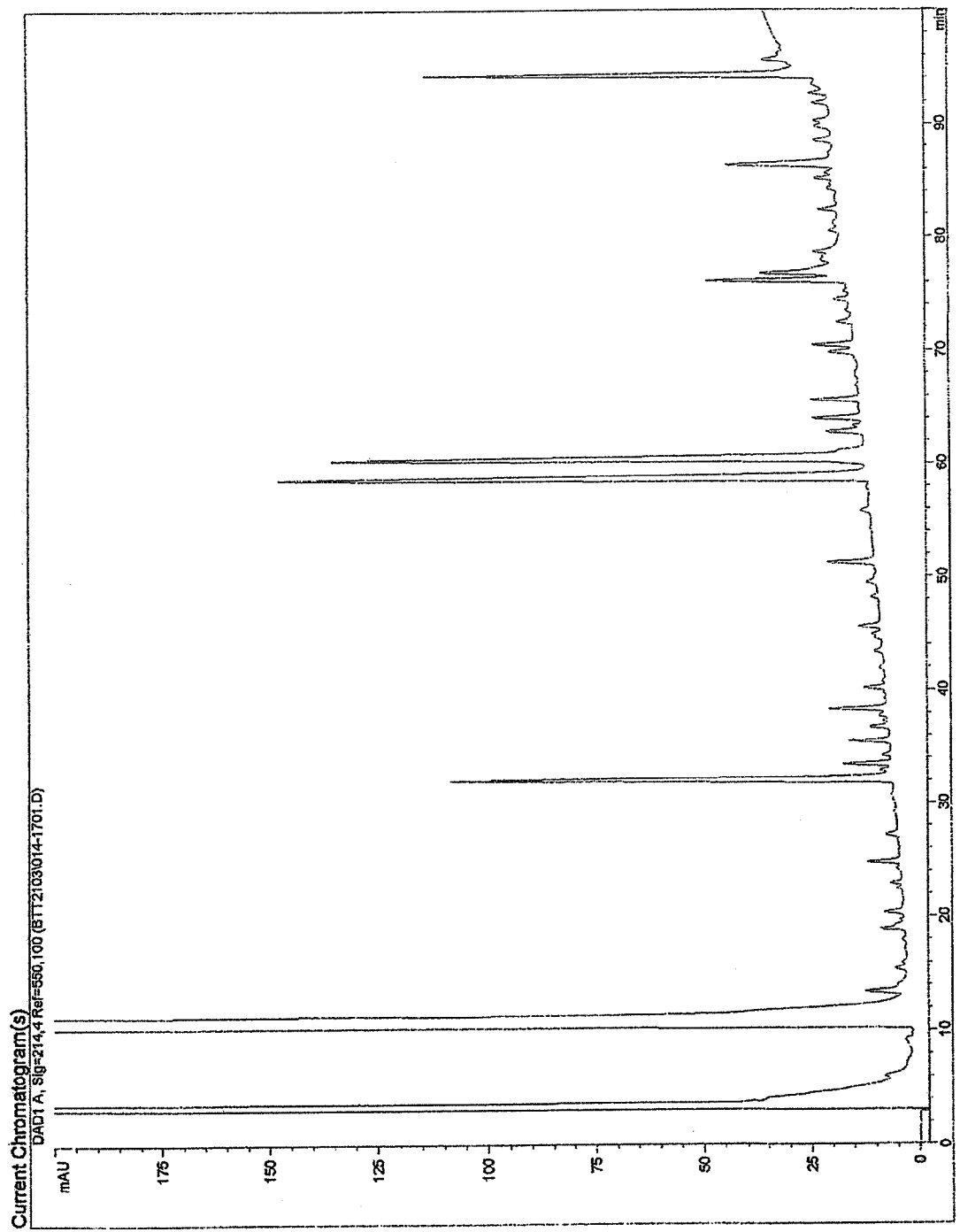
Fig. 2.1

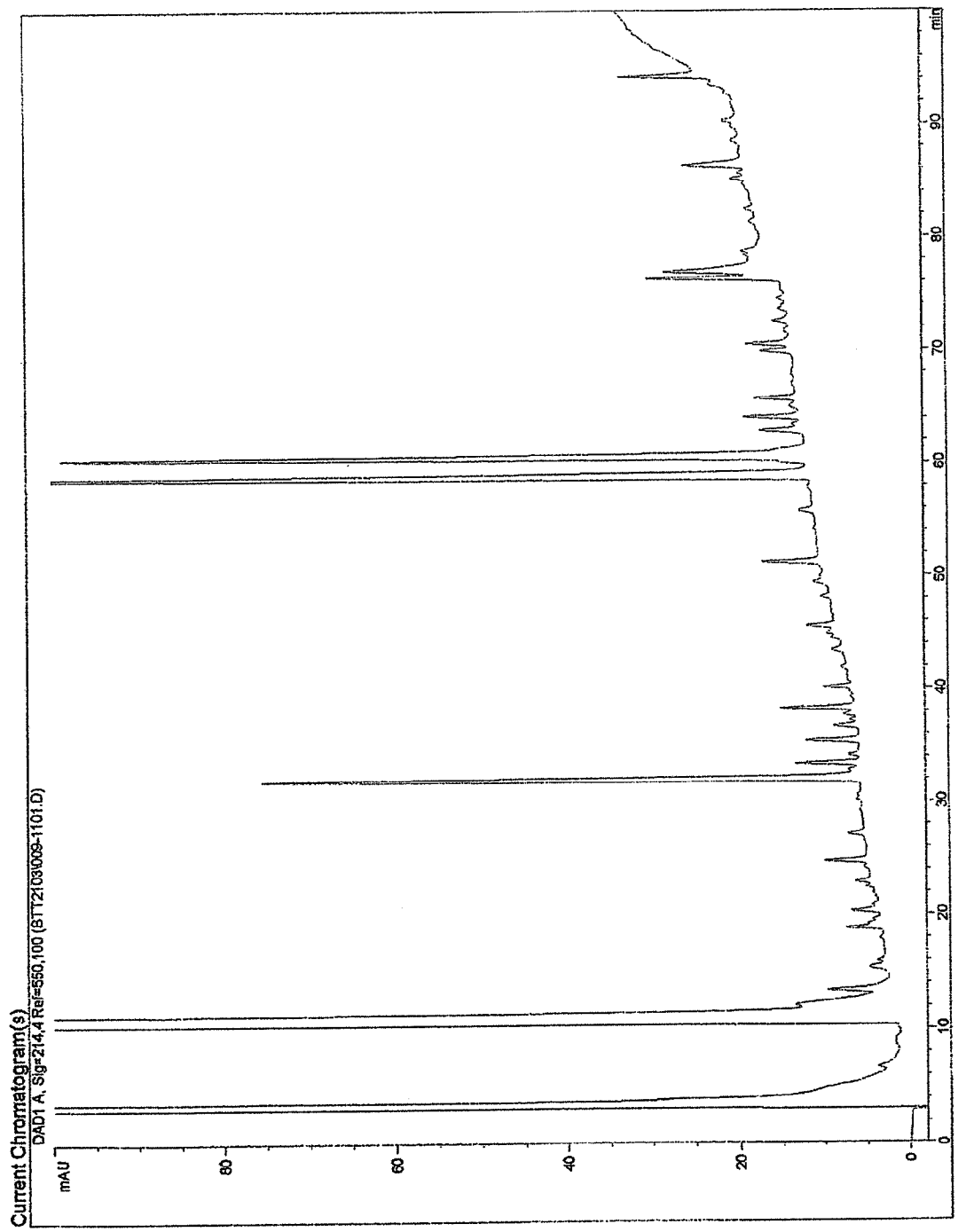
Fig.2.2

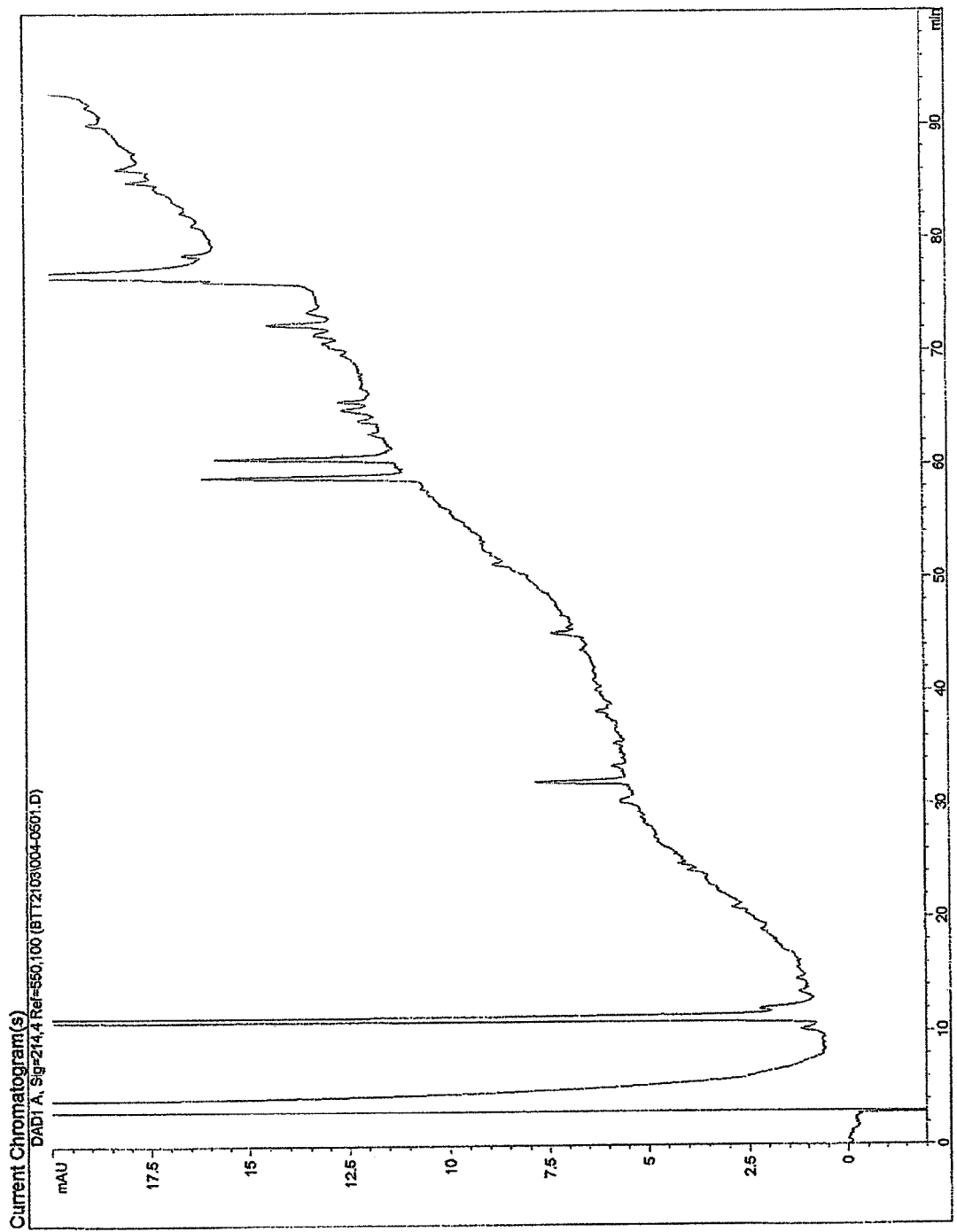
Fig. 2.3

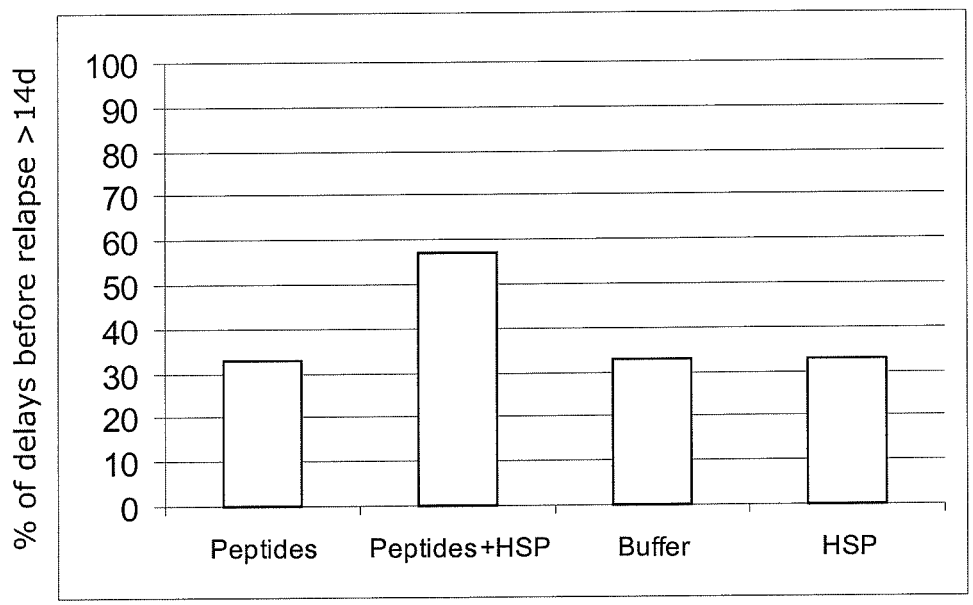
Fig.3.1
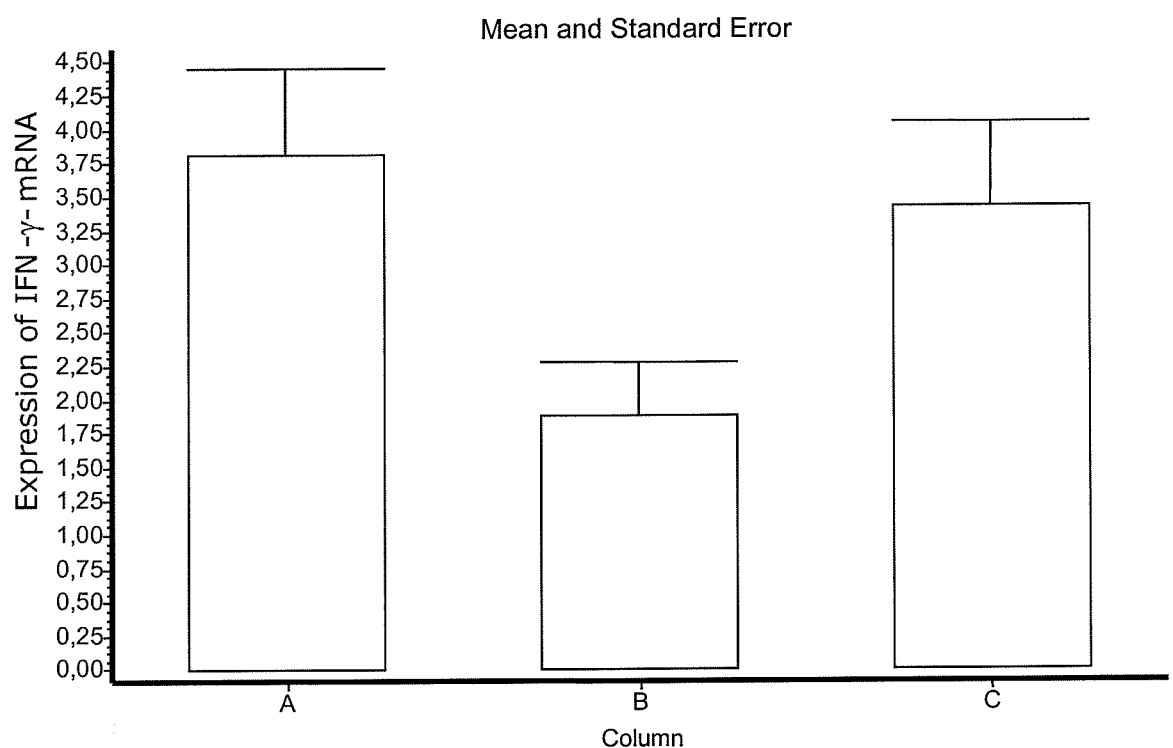
Fig.3.2

PEPTIDE COMPLEX

The present invention relates to complexes of heat shock proteins and tolerogenic peptides.

It is known that complexes of peptides together with heat shock proteins are suitable for inducing tolerance.

U.S. Pat. No. 6,312,711 discloses a pharmaceutical or food composition intended for treating pathologies associated with graft rejection or an allergic or autoimmune reaction comprising the administration of a complex of a stress protein and epitopes of an antigenic structure.

Surprisingly, the inventors of the present invention have been able to isolate small peptides which in complex with heat shock proteins are especially useful for prevention or treatment of allergy, graft rejection or autoimmune diseases.

The inventors identified the following sequences

```
GFFYTPK (insulin 23-29)            SEQ ID No 1

GFFYTPKT (insulin 23-30)           SEQ ID No 2

IYPPNANK (DER p1)                  SEQ ID No 3

GIEYIQHNGVVQESYYR (DER P1)         SEQ ID No 4

ASTTTNYT (gp120 of HIV)            SEQ ID No 5

DYEYLINVIHAFQYV (PLP 56-70)        SEQ ID No 6

EKLIETYFSKNYQDYEYLINVI (PLP 43-64) SEQ ID No 7

KTTICGKGLSATVT (PLP 104-117)       SEQ ID No 8

HSLGKWLGHPDKF (PLP 139-151         SEQ ID No 9
C¹⁴⁰ → S¹⁴⁰)

PRHPIRVELPCRISP (MOG 8-22)         SEQ ID No 10

DEGGYTCFFRDHSYQ (MOG 92-106)       SEQ ID No 11

Ac-ASQKRPSQRHG (MBP ac1-11)        SEQ ID No 12

TGILDSIGRFFSG (MBP 35-47)          SEQ ID No 13

VHFFKNIVTPRTP (MBP 89-101)         SEQ ID No 14

HCLGKWLGHPDKF (PLP 139-151)        SEQ ID No 15

MEVGWYRSPFSRVVHLYRNGK (MOG)        SEQ ID No 16

QKRAAYDQYGHAAFE (E. Coli DnaJ)     SEQ ID No. 17

QKRAAVDTYCRHNYG (HLA DRB1*0401)    SEQ ID No. 18

QRRAAYDQYGHAAFE                    SEQ ID No. 19
and

QRRAAVDTYCRHNYG                    SEQ ID No. 20.
```

DER: *Dermatophagoides pteronyssinus*
PLP: proteolipid protein
MOG: myelin oligodendrocyte glycoprotein
MBP: myelin basic protein
HLA: human leukocyte antigen Especially useful are sequences having the sequence $$R_1\text{-QXRAA-}R_2$$

with
$R_1$=peptide with 1-10 amino acids
$R_2$=peptide with 1-10 amino acids
X=K or R.

Preferably these sequences are prepared by hydrolysis of natural occurring peptides or proteins.

In one aspect of the invention, the invention provides a complex comprising at least one heat shock protein (HSP) and at least one peptide selected from Seq. ID Nos. 1 to 20 or having the sequence $$R_1\text{-QXRAA-}R_2$$

with
$R_1$=peptide with 1-10 amino acids
$R_2$=peptide with 1-10 amino acids
X=K or R.

In a preferred embodiment, the HSP is a bacterial HSP and more preferably a bacterial HSP from a saprophytic bacteria. Suitable HSP can be selected from hsp40, hsp70, grpE, hsp90, CPN60 (hsp60), FK506-binding proteins, gp96, calrecticulin, hsp110, grp170 and hsp100, alone or in combination.

According to the invention either complete HSP or fragments of the HSP can be used. A preferred fragment is the polypeptide binding domain of the heat shock protein.

Another aspect of the invention is a nucleic acid encoding at least one of the peptides having Seq. ID Nos. 1 to 20 or having the sequence $$R_1\text{-QXRAA-}R_2$$

with
$R_1$=peptide with 1-10 amino acids
$R_2$=peptide with 1-10 amino acids
X=K or R.

In a further aspect, the invention provides a nucleic acid encoding at least one HSP and at least one peptide comprising at least one of the sequences selected from Seq. ID No. 1 to Seq. ID No. 20 or having the sequence $R_1$-QXRAA-$R_2$ with $R_1$=peptide with 1-10 amino acids, $R_2$=peptide with 1-10 amino acids, X=K or R. This nucleic acid can be used to express the corresponding peptide in vitro or in a cell or in a patient. For expression in a patient, a gene delivery vehicle would be necessary. Therefore, the gene delivery vehicle comprising at least the nucleic acid of the invention is also part of the invention.

Such a gene delivery vehicle would transfect a cell. Therefore, a cell transfected by at least one gene delivery vehicle of the invention is also part of the invention.

Either the complex or the gene delivery vehicle could be administered to patient in need thereof. Therefore, a pharmaceutical or food composition comprising the complex or the gene delivery vehicle of the present invention is also an aspect of the invention.

The complex of the present invention can be prepared by hydrolyzing in-vitro at least one protein with at least one protease to obtain hydrolyzed fragments and combining in-vitro the hydrolyzed fragments with at least one heat shock protein to obtain at least one complex.

Alternatively, the complex of the present invention can be prepared by synthesizing the peptides identified as Seq. ID No. 1 to Seq. ID No. 20 or having the sequence sequence $R_1$-QXRAA-$R_2$ with $R_1$=peptide with 1-10 amino acids, $R_2$=peptide with 1-10 amino acids, X=K or R and combining the synthesized peptide with at least one heat shock protein. Suitable procedures are described by Merrifield, 1963, J. Am. Chem. Soc. 85:2149.

In a preferred embodiment, the peptide-HSP complex is formed under reducing conditions in a buffer containing at least one reducing agent. Suitable reducing agents are for example dithiothreitol and beta-mercaptoethanol. The most preferred concentrations of the reducing agent are from 0.001 mM to 700 mM, and more preferably between 0.1 mM and 50 mM.

In another embodiment, the peptide-HSP complex is formed under oxidative conditions in a buffer containing at least one oxidative agent. A suitable oxidative agent is for example hydrogen peroxide. The most preferred concentrations of the oxidative agent are from 0.1 mM to 100 mM, and more preferably between 0.5 mM and 20 mM.

In another preferred embodiment, the peptide-HSP complex is formed in a buffer which contains neither a reducing agent nor an oxidative agent.

A further aspect of the invention is to use the complex of the present invention as a carrier for the delivery of biologically active molecules. The peptides can be linked to biologically active molecules e.g. nucleic acids, peptides, polypeptides, proteins, polysaccharides, lipids, drugs, and can then be combined with the heat shock protein.

In a further aspect the invention provides the isolated peptide selected from the group consisting of

| | |
|---|---|
| GFFYTPK (insulin 23-29) | SEQ ID No 1 |
| GFFYTPKT (insulin 23-30) | SEQ ID No 2 |
| IYPPNANK (DER p1) | SEQ ID No 3 |
| GIEYIQHNGVVQESYYR (DER P1) | SEQ ID No 4 |
| ASTTTNYT (gp120 of HIV) | SEQ ID No 5 |
| DYEYLINVIHAFQYV (PLP 56-70) | SEQ ID No 6 |
| EKLIETYFSKNYQDYEYLINVI (PLP 43-64) | SEQ ID No 7 |
| KTTICGKGLSATVT (PLP 104-117) | SEQ ID No 8 |
| HSLGKWLGHPDKF (PLP 139-151 $C^{140} \rightarrow S^{140}$) | SEQ ID No 9 |
| PRHPIRVELPCRISP (MOG 8-22) | SEQ ID No 10 |
| DEGGYTCFFRDHSYQ (MOG 92-106) | SEQ ID No 11 |
| Ac-ASQKRPSQRHG (MBP ac1-11) | SEQ ID No 12 |
| TGILDSIGRFFSG (MBP 35-47) | SEQ ID No 13 |
| VHFFKNIVTPRTP (MBP 89-101) | SEQ ID No 14 |
| HCLGKWLGHPDKF (PLP 139-151) | SEQ ID No 15 |
| MEVGWYRSPFSRVVHLYRNGK (MOG) | SEQ ID No 16 |
| QKRAAYDQYGHAAFE (E. Coli DnaJ) | SEQ ID No. 17 |
| QKRAAVDTYCRHNYG (HLA DRB1*0401) | SEQ ID No. 18 |
| QRRAAYDQYGHAAFE | SEQ ID No. 19 |
| QRRAAVDTYCRHNYG | SEQ ID No. 20 | and $R_1$ - QXRAA - $R_2$ with
$R_1$=peptide with 1-10 amino acids
$R_2$=peptide with 1-10 amino acids
X=K or R.

Also a complex of these peptides with at least one other protein such as but not limited to antibodies is part of the invention.

The complex of the present invention or the gene delivery vehicle of the invention are useful for the prevention or treatment of allergy, graft rejection or autoimmune diseases.

The complex of the present invention can also be used for the induction of a cellular reponse comprising cells able to secrete immunosuppressive cytokines after exposure to at least one antigen comprising at least one sequence selected from SEQ ID No 1 to SEQ ID No 20 or comprising the sequence $R_1$-QXRAA-$R_2$ with $R_1$=peptide with 1-10 amino acids, $R_2$=peptide with 1-10 amino acids, X=K or R.

A further aspect of the invention is a diagnostic composition comprising the complex of the invention.

A further aspect of the invention is a method for the in vitro diagnosis of a disease comprising the steps of
bringing a biological fluid of an animal containing proteins into contact with the diagnostic composition of the invention
measuring binding of said proteins with said diagnostic composition
wherein binding indicates a disease of the animal.

Another aspect of the invention is to provide with antibodies specific for at least one of the peptides of the inventions or specific for at least one complex of the present invention. The antibody can be a polyclonal antibody, a monoclonal antibody or fragments of such as but not limited to Fab and F(ab')$_2$.

The antibody of the present invention can be used for the prevention or treatment of allergy, graft rejection or autoimmune disease. Also the antibody of the present invention can be used in a method for the in vitro diagnosis of a disease such as allergy, graft rejection or autoimmune disease.

As an alternative to direct administration of the heat shock protein peptide complex, one or more polynucleotide constructs may be administered which encode heat shock protein and target peptide In expressible form. The expressible polynucleotide constructs are introduced into cells using in vivo or in vitro methods.

Amino-acid sequences and nucleotides sequences of HSP and target proteins are generally available in sequences databases such as GenBank and Swiss-Prot.

DNA sequences can be amplified from genomic or cDNA by PCR using specific primers designed from the known sequences. "PCR" refers to the technique of polymerase chain reaction as described in Saikl, et al., Nature 324:163 (1986); and Scharf et al., Science (1986) 233:1076-1078; and U.S. Pat. Nos. 4,683,195; and 4,683,202. A nucleotide sequence encoding a polypeptide of any desired length can be generated by PCR. PCR can be carried out e.g. by use of a thermal cycler and a thermo-resistant DNA polymerase.

The HSP-peptide fusion protein of the invention incorporates one peptide and one heat shock protein, optionally separated by a peptide linker. Various methods for production of fusion proteins are well known in the state of the art. One suitable technique utilizes initial separate PCR amplification reactions to produce separate DNA segments encoding the two sequences, each with a linker segment attached to one end, followed by fusion of the two amplified products in a further PCR step. This technique is referred to as linker tailing. Suitable restriction sites may also be engineered into regions of interest, after which restriction digestion and ligation is used to produce the desired HSP-peptide fusion protein encoding sequence.

Methods of incorporating particular nucleic acids into expression vectors are well known to those of skill in the art, but are described in detail in, for example, Sambrook et al., Molecular Cloning: A Laboratory Manual ($2^{nd}$ ed.), Vols. 1 to 3, Cold Spring Harbor Laboratory, (1989) or Current Protocols in Molecular Biology, F. Asubel et al., ed. Green Publishing and Wiley-Interscience, New York (1987). To construct an expressible polynucleotide, a region encoding the heat shock protein and peptide is prepared as discussed above and inserted into a mammalian expression vector operatively linked to a suitable promoter such as the SV40 promoter, the cytomegalovirus (CMV) promoter or the Rous sarcoma virus (RSV) promoter. The resulting construct may then be used as a vaccine for genetic immunization. The nucleic acid polymer(s) could also be cloned into a viral vector. Suitable vectors include but are not limited to retroviral vectors, adenovirus vectors, vaccinia virus vectors, pox virus vectors and adenovirus-associated vectors.

Alternatively, a polynucleotide containing a sequence encoding the HSP and a gene encoding a desired peptide may be introduced respectively into two different vectors each capable of coexistence and replication in the same host.

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, complexation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

EXAMPLES

Protein Preparation

Before enzymatic digestions, the proteins of interest are extensively washed with water by centrifugation through a centricon YM-03 or YM-10 assembly to remove any low molecular weight material loosely associated with it.
Trypsin Digestion One to five milligrams of the protein of interest is dissolved in 1 to 5 mL of phosphate buffer 40 mM pH 8.0 (final concentration of 1 mg/mL). The solution is incubated for 10 minutes at 100° C. The solution is then rapidly cooled at 4° C., and 18 to 90 µL of β-mercaptoethanol is added (1.8% v/v). The resulting solution is incubated at 37° C. for 10 minutes and 20 to 100 µL of trypsin solution (10 mg/mL of Tris.HCl 40 mM pH 8.0; final ratio (w/w) protease/protein of 1:100) is added to the protein solution.

The resulting solution is incubated at 37° C. for six hours. The solution is then centrifuged through a centricon YM-10 assembly to remove the remaining protein and trypsin.
DnaK.ATP Complex Preparation 25 µL of ATP solution (4.5 mg/mL of buffer 1 (25 mM HEPES, 10 mM KCl, 3 mM magnesium chloride, 5 mM beta-mercaptoethanol, pH 7.5) is added to 400 µL of DnaK (2 mg/mL of buffer 1). The solution is incubated at 20° C. for one hour, and then centrifuged through a centricon YM-10 assembly to remove any low molecular weight material loosely associated with DnaK. The large molecular weight fraction is removed, and washed extensively with buffer 1 by ultrafiltration using a centricon YM-10.
In vitro Production of Stress Protein-peptide Complexes. Isolation of the Bound Peptides The ultrafiltrated trypsin digestion is mixed with the ATP-pre-treated DnaK to give at least a 1:1 (w:w) DnaK:peptides ratio. Then, ADP is added (1 mM final) and the mixture is incubated for at least one hour at 25° C. in the suitable buffer 1. The preparations are centrifuged through a centricon YM-10 assembly to remove the remaining unbound peptides. The low and the large molecular weight fractions are recovered. The large molecular weight fraction containing DnaK-peptide complexes is washed extensively with buffer 1 containing 1 mM ADP by ultrafiltration using a centricon YM-10. The bound peptides are eluted by incubating the HSP-peptide complexes in a low pH buffer. A last ultrafiltration using a centricon YM-10 is removing the large molecular weight fraction.
HPLC Analysis The resulting low molecular weight fractions are fractionated by reverse phase high pressure liquid chromatography (HPLC) using a Vydac C18 reverse phase column (HP32, 201TP52 C18, 250/2.1 mm, 5 µm (available from Vydac)). The elution of the peptides can be monitored at both OD 214 nm and OD 280 nm.
Biological Studies It is a model wherein NOD (Not Obese Diabetic) mice are treated after the onset of the auto-immune disease.

After the onset of the first signs of diabetes, 500 normal Langerhans islets from young NOD mice are grafted under the renal capsule of diabetic animals. Glycosuria and glycemia are then monitored daily. Mice are considered diabetic when a glucosuria is detected and glycemia exceeds 12 mmole/L (2.16 g/L) during two consecutive days. The first day of hyperglycemia is considered as the start of relapse.
Treatment of Mice All treatments were started on the first day after the onset of the disease, that is the day before transplantation. Mice were treated by sublingual injections, one dose each two days, to achieve the total doses:
Group 1: Peptides (1 µg)+HSP (1 µg)
Group 2: Peptides (1 µg)
Group 3: HSP (1 µg)
Group 4: buffer
Clinical Outcomes In non-treated NOD mice, the average delay before a relapse occurs is about 11 to 12 days. Considering that a delay exceeding 14 days results from a therapeutic effect, one notices that, in the group treated with complexes, the proportion of delays exceeding 14 days is 4/7 (57%). In the other group treated with either peptides, buffer or HSP alone, the proportion is 2/6 (33%). Thus, there is a therapeutic effect of the combination between an HSP and peptides given orally.

The mRNAs of interferon-γ and IL-4 have been assayed by PCR amplification in various tissues: the graft, the spleen and, as a control, the kidney. The results are expressed as ratios of the amount of interferon-γ mRNA vs the amount of actine mRNA. IL-4 was not detected in any sample, whereas Interferon-γ was found in the spleen at levels that were rather similar in all the groups.

In contrast, some interesting differences were observed in the grafted islets. The level of interferon-γ was significantly lower in the group treated with peptides-HSP complexes. It is thus possible that the complexes had induced in the Peyer's patches regulatory T cells that, after their migration into the graft, have inhibited the $T_H1$ cells that contribute to the destruction of the grafted islets by secreting cytokines such as interferon-γ.

FIGURES

FIG. 1.1: peptides (MW< or =10 kDa) generated by trypsin-cleavage of Derp1.

FIG. 1.2: unbond peptides (MW< or 10 kDa) to DnaK, from the trypsin-cleavage of Derp1.

FIG. 1.3: peptides from the trypsin-cleavage of Derp1 (MW< or =10 kDa) that were bound to DnaK.

FIG. 2.1: peptides (MW< or 10 kDa) generated by trypsin-cleavage of insulin.

FIG. 2.2: unbound peptides (MW< or 10 kDa) to DnaK, from the trypsin-cleavage of insulin.

FIG. 2.3: peptides from the trypsin-cleavage of insulin (MW< or =10 kDa) that were bound to DnaK.

FIG. 3.1: proportion of delays before relapse exceeding 14 days.

FIG. 3.2: expression of IFNγ mRNA in the grafted islets. A: group 2 (peptides); B: group 1 (HSP+peptides); C: buffer.

The invention claimed is:

1. A non-covalent complex comprising at least one heat shock protein (HSP) and a peptide consisting of GFFYTPKT (insulin 23-30)            SEQ ID No 2.

2. The non-covalent complex according to claim 1, wherein the HSP is a bacterial HSP.

3. The non-covalent complex according to claim 1, wherein the HSP is selected from the group consisting of hsp40, hsp70, grpE, hsp90, CPN60 (hsp60), FK506-binding proteins, gp96, calrecticulin, hsp110, grp170 and hsp100.

4. The non-covalent complex according to claim 1, wherein the heat shock protein is the polypeptide binding domain of a heat shock protein.

5. A pharmaceutical or food compositions comprising the non-covalent complex of claims 1.

6. A method for preparing a non-covalent complex according to claim 1 comprising the steps of
  hydrolyzing in-vitro an insulin protein with trypsin to obtain hydrolyzed fragments comprising the peptide consisting of SEQ ID NO: 2; and
  combining in-vitro the hydrolyzed fragments with at least one heat shock protein to obtain a complex.

7. The method of claim 6, wherein unbound hydrolyzed fragments are separated from the non-covalent complex.

8. A diagnostic composition comprising the non-covalent complex of claim 1.

9. The non-covalent complex of claim 1 wherein the heat shock protein is hsp70.

* * * * *

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:insulin
      23-29 peptide

<400> SEQUENCE: 1

Gly Phe Phe Tyr Thr Pro Lys
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:insulin
      23-30 peptide

<400> SEQUENCE: 2

Gly Phe Phe Tyr Thr Pro Lys Thr
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:DER p1
      peptide

<400> SEQUENCE: 3

Ile Tyr Pro Pro Asn Ala Asn Lys
 1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence:DER p1
      peptide

<400> SEQUENCE: 4

Gly Ile Glu Tyr Ile Gln His Asn Gly Val Val Gln Glu Ser Tyr Tyr
 1               5                  10                  15

Arg

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:gp120 of HIV
      peptide

<400> SEQUENCE: 5

Ala Ser Thr Thr Thr Asn Tyr Thr
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:PLP 56-70 peptide

<400> SEQUENCE: 6

Asp Tyr Glu Tyr Leu Ile Asn Val Ile His Ala Phe Gln Tyr Val
 1               5                   10                  15

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence:PLP 43-64 peptide

<400> SEQUENCE: 7

Glu Lys Leu Ile Glu Thr Tyr Phe Ser Lys Asn Tyr Gln Asp Tyr Glu
 1               5                   10                  15

Tyr Leu Ile Asn Val Ile
            20

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:PLP 104-117 peptide

<400> SEQUENCE: 8

Lys Thr Thr Ile Cys Gly Lys Gly Leu Ser Ala Thr Val Thr
 1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:PLP 139-151
      C140 -> S140 peptide

<400> SEQUENCE: 9

His Ser Leu Gly Lys Trp Leu Gly His Pro Asp Lys Phe
 1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:MOG 8-22 peptide

<400> SEQUENCE: 10

Pro Arg His Pro Ile Arg Val Glu Leu Pro Cys Arg Ile Ser Pro
 1               5                   10                  15

<210> SEQ ID NO 11
<211> LENGTH: 15
<212> TYPE: PRT
<213> ORGANISM: Artificial Sequence

```
<220> FEATURE:
<223> OTHER INFORMATION: Description of Artificial Sequence:MOG 92-106
      peptide

<400> SEQUENCE: 11

Asp Glu Gly Gly Tyr Thr Cys Phe Phe Arg Asp His Ser Tyr Gln
 1               5                  10                  15

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:MBP ac1-11
      peptide
<220> FEATURE:
<221> NAME/KEY: MOD_RES
<222> LOCATION: (1)
<223> OTHER INFORMATION: ACETYLATION

<400> SEQUENCE: 12

Ala Ser Gln Lys Arg Pro Ser Gln Arg His Gly
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:MBP 35-47
      peptide

<400> SEQUENCE: 13

Thr Gly Ile Leu Asp Ser Ile Gly Arg Phe Phe Ser Gly
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:MBP 89-101
      peptide

<400> SEQUENCE: 14

Val His Phe Phe Lys Asn Ile Val Thr Pro Arg Thr Pro
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:PLP 139-151
      peptide

<400> SEQUENCE: 15

His Cys Leu Gly Lys Trp Leu Gly His Pro Asp Lys Phe
 1               5                  10

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence:MOG peptide

<400> SEQUENCE: 16

Met Glu Val Gly Trp Tyr Arg Ser Pro Phe Ser Arg Val Val His Leu
```

```
                1               5              10              15

Tyr Arg Asn Gly Lys
                20

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence:E. Coli DnaJ
      peptide

<400> SEQUENCE: 17

Gln Lys Arg Ala Ala Tyr Asp Gln Tyr Gly His Ala Ala Phe Glu
  1               5              10              15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:HLA
      DRB1*0401 peptide

<400> SEQUENCE: 18

Gln Lys Arg Ala Ala Val Asp Thr Tyr Cys Arg His Asn Tyr Gly
  1               5              10              15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 19

Gln Arg Arg Ala Ala Tyr Asp Gln Tyr Gly His Ala Ala Phe Glu
  1               5              10              15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 20

Gln Arg Arg Ala Ala Val Asp Thr Tyr Cys Arg His Asn Tyr Gly
  1               5              10              15
```